(12) United States Patent
Colantonio et al.

(10) Patent No.: US 8,728,056 B2
(45) Date of Patent: May 20, 2014

(54) APPARATUS AND METHOD FOR STERILE DOCKING OF MALE MEDICAL LINE CONNECTORS

(75) Inventors: Anthony J. Colantonio, Meadville, PA (US); Menno D. Jager, Meadville, PA (US)

(73) Assignee: PSI MedicaL Catheter Care, LLC, Erie, PA (US)

( * ) Notice: Subject to any disclaimer, the term of this patent is extended or adjusted under 35 U.S.C. 154(b) by 877 days.

(21) Appl. No.: 12/590,369

(22) Filed: Nov. 6, 2009

(65) Prior Publication Data

US 2010/0057054 A1 Mar. 4, 2010

Related U.S. Application Data

(63) Continuation-in-part of application No. 12/074,951, filed on Mar. 7, 2008, now Pat. No. 8,083,729.

(60) Provisional application No. 61/002,173, filed on Nov. 7, 2007.

(51) Int. Cl.
| | | |
|---|---|---|
| *A61M 25/16* | (2006.01) | |
| *A61M 25/18* | (2006.01) | |
| *A61M 39/02* | (2006.01) | |
| *A61M 39/00* | (2006.01) | |
| *A61M 39/10* | (2006.01) | |

(52) U.S. Cl.
USPC ........... 604/539; 604/533; 604/534; 604/535; 604/905

(58) Field of Classification Search
USPC ........... 128/912, DIG. 6, DIG. 26; 604/93.01, 604/246, 256, 265, 533, 534, 535, 537, 539, 604/905, 48, 248
See application file for complete search history.

(56) References Cited

U.S. PATENT DOCUMENTS

| | | | | |
|---|---|---|---|---|
| 4,440,207 A | * | 4/1984 | Genatempo et al. | 150/154 |
| 5,310,524 A | * | 5/1994 | Campbell et al. | 422/33 |
| 5,336,180 A | * | 8/1994 | Kriesel et al. | 604/82 |
| 5,792,120 A | * | 8/1998 | Menyhay | 604/256 |
| 6,911,025 B2 | * | 6/2005 | Miyahara | 604/415 |

* cited by examiner

*Primary Examiner* — Kevin C Sirmons
*Assistant Examiner* — Shefali Patel
(74) *Attorney, Agent, or Firm* — Carothers and Caroters

(57) ABSTRACT

A docking station for maintaining sterilization of temporarily disconnected male medical line connectors. The docking station has a plurality of docking bays, each of which retain an ampule therein containing a sterilization fluid and has an access mouth exteriorly exposed when the ampule is secured in its respective bay. The mouth of the ampule is provided with a female medical line connection for temporarily receiving and securing one of the male medical line connector temporarily disconnected from a patient. A tubular tip and a concentric connection collar of the one of the male medical line connector is thereby immersed in the sterilization fluid for sterilization while docked. Each of the ampules is secured against rotation in a clockwise direction in their respective docking bay to facilitate threadable connection of one of the male medical line connector. However, the ampules are permitted to freely rotate in the counterclockwise direction in their respective bays to prevent disconnection of one of the male medical line connectors therefrom while the connected ampules are retained in their respective bays. This prevents accidental reuse of an ampule. The ampules are provided with laterally extending wings which are received in recesses in their respective bays. The recesses have inclined ramp surfaces for engaging the bottom of the wings and thereby ejecting the ampules out of the bays when rotated in the counterclockwise direction.

6 Claims, 15 Drawing Sheets

APPARATUS AND METHOD FOR STERILE DOCKING OF MALE MEDICAL LINE CONNECTORS

CROSS REFERENCE

This application is a continuation-in-part of U.S. application Ser. No. 12/074,951, filed on 7 Mar. 2008 now U.S. Pat. No. 8,083,729, and entitled APPARATUS AND METHOD FOR STERILE DOCKING OF MALE MEDICAL LINE CONNECTORS, which claims the benefit of U.S. Provisional Application No. 61/002,173, filed on Nov. 7, 2007, and entitled DOCKING STATION FOR THE TEMPORARY STERILE SECUREMENT AND SIMULTANEOUS DISINFECTION OF MEDICAL INFUSION TUBING.

FIELD OF THE INVENTION

The present invention relates to the field of medical liquid administration, and more particularly, to a docking apparatus and method for simultaneously enhancing the sterility, temporary securement and disinfection of disconnected medical infusion tubing during periods of non-use.

BACKGROUND OF THE INVENTION

Improvements in patient safety have been among the primary concerns of many efforts in today's healthcare industry. Healthcare associated infections remain a major area of focus for these efforts. The Center for Disease Control and Prevention cites healthcare associated infections in the top ten leading causes of death in the United States. Annually, healthcare associated infections account for an estimated 1.7 million infections in hospitals, 99,000 associated deaths, and 4.5 to 5.7 billion dollars in added patient care costs.

The reduction of healthcare associated infections depends upon awareness and adherence to aseptic technique when handling medical equipment that comes into direct contact with a patient. Medical equipment is constantly threatened by exposure to surrounding contaminated surfaces. These surfaces contain microorganisms (bacteria) which can easily adhere to the surface of medical equipment. Once contaminated, the medical equipment becomes a danger to the patient and can serve as a silent killer. Healthcare institutions use millions of intravenous catheters each year. These catheters are at risk of contamination by a variety of mechanisms. One such mechanism relates to the contamination of the exposed tip of an intravenous administration set. This particular problem arises when an intravenous infusion line is temporarily disconnected from a patient (a process which can occur multiple times per day for an individual patient). During the time that the infusion line is disconnected from the patient, the exposed tip of the intravenous tubing may contact potential contaminants. These contaminants can then lead to infection within a patient's bloodstream once the infusion tubing is reconnected to the patient.

The critical event in the aforementioned circumstance is the failure to retain the sterility of the infusion tubing tip and failure to adequately disinfect the tip in the instance of inadvertent contamination during the time of disconnect from the patient. This risk is, in part, an unanticipated outcome of the somewhat recent implementation of needle-less intravenous systems. Prior to the introduction of these needle-less systems, healthcare practitioners typically replaced the needle used to connect the infusion tubing to the intravenous tubing with a new sterile, capped needle to prevent contamination when the line was hanging between uses. Currently, many practitioners are not actively considering the risk of contamination and are not taking steps to secure the sterility of the exposed tubing. When efforts are made to maintain the sterility of the exposed tubing tip, these efforts are both cumbersome (and therefore at times skipped over), or they fail due to technical shortcomings.

Safe practice recommendations include the use of aseptic technique when handling medical infusion lines. The aseptic technique, as pertains specifically to intravenous catheters, includes covering the exposed end of intravenous tubing used for intermittent infusions with a sterile cap between uses and to disinfect the cap prior to reattachment to a patient. There currently exists a plain sterile cap for intravenous infusion tubing that is individually packaged. These caps have shortcomings which limit their routine use. Specifically, these caps must be opened from their individual wrappers for use. This process itself can place the cap at risk for infection before it is even placed onto the intravenous tubing as it requires significant manipulation by the practitioner. In addition, the practitioner may not have one of the individual wrappers immediately available when needed. Furthermore, these caps do not accomplish any active disinfection of the intravenous tubing tip surface.

Disinfecting the surfaces of medical equipment with alcohol is a well accepted and established practice. Evidence exists supporting the use of a one minute alcohol immersion as adequate disinfectant technique. Current practice often utilizes alcohol cloth swabs to accomplish the task of disinfecting the surface of medial equipment, including intravenous tubing. This method has faults limiting its use. The exposure of the intravenous tubing tip to the cloth swab of alcohol does not qualify as an immersion technique. Also, the practitioner may be very likely to contaminate the tubing tip with their skin which is surrounding the cloth swab as it is being held. Lastly, the alcohol prep pads containing the cloth swabs may not be immediately available for use at the time of greatest need.

The docking station herein disclosed includes a means to temporarily and safely secure the free tip of intravenous tubing (or any other medical infusion line) while simultaneously disinfecting that same tip. In this way, the device and associated method described will adequately provide a means to maintain the sterility of a reusable intravenous administration set (or other medical infusion line) that has been disconnected from a patient until it is ready to be reattached for future use. In addition, the docking station of the present invention further provides a means for ensuring that the device utilized to temporarily store and sterilize the medical line connectors cannot be reused.

SUMMARY OF THE INVENTION

The docking station of the present invention for male medical line connectors, such as, but not limited to, IV connectors, indwelling nerve catheters and dialysate connectors, is comprised of a base housing that is securable to a stationary surface and has a plurality of docking bays. Each of the docking bays are dimensioned and contoured for respectively receiving and temporarily retaining capsules or ampules containing sterilization fluid, such an alcohol liquid or gel. Each of the ampules has a chamber therein containing the sterilization fluid and an access mouth which is exteriorly exposed when the ampule is secured in one of the bays. The mouth of the ampule has a female medical line connection, such as a luer lock mechanism, dimensioned and contoured for temporarily receiving and securing a male medical line connector thereto with the tubular tip of the male connector thereby immersed in the sterilization fluid.

When it is time to reconnect the male medical line connector, it is pulled, along with the connected ampule, from the docking station bay by pulling the connected male connector. Thereafter the male connector is disconnected from the ampule for reconnection to the patient and the used ampule is discarded.

A removable sterilization cover may be provided over each of the ampule mouths or each of the bays of the docking station.

The ampules are received respectively in the bays of the docking station by push insert and pull removal. The ampules in a preferred embodiment are respectively received each in a socket provided in the respective bays with a friction fit for retaining the ampules respectively in the bays. This friction fit may also additionally be provided with a snap fit if desired.

The ampules are secured against rotation in the bays whereby the male connectors may be rotatably connected to the respective ampules. To provide this securement against rotation, the ampules and bays have inter-engaging parts whereby the ampules are secured against rotation in the respective bays.

The base housing of the docking station may be slidably received in a holster which in turn is secured to a normally stationary vertical surface, such as an IV pole.

Normally the base will be provided in rows on the base housing and the rows may in addition be designated by color coding to match a corresponding male medical line connector type.

Absorbent material, such as foam, compressible sponge, fiber or fabric, may also be provided in the ampules for absorbing and retaining the sterilization fluid. In addition, the ampule mouths may be sealed with a pierceable membrane for piercing by the tubular tip of the male connector when it is secured to the female connection of the ampule.

To further ensure that an ampule containing sterilization fluid which has already been used once to secure and sterilize a male medical line connector, it cannot be used again the second time, the ampules are secured against rotation in the clockwise direction in their respective bays to facilitate total connections of a male medical line connector, but are, however, permitted to freely rotate in a counterclockwise direction in their respective bays to prevent disconnection of a male medical line connector therefrom while the connected ampule is retained in its respective of said bays. To accomplish this, the ampules and bays have inter-engaging parts whereby the ampules are secured against rotation in the clockwise direction in their respective bays and permitted to freely rotate in the counterclockwise direction. These inter-engaging parts include latterly extending wings provided on the ampules and corresponding recesses in the respective bays receiving the wings. The recesses have ramp surfaces for engaging bottom edges the wings whereby the ampules are forced out of their respective bays when rotated in the counterclockwise direction. This forces the user to remove the respective ampule from its respective bay in the docking station so that the ampule does not remain in the docking station. In this manner, another operator cannot be confused into thinking that the ampule is fresh, sterile and ready to use. It forces the original operator to discard the used ampule. In addition, the respective bays are positioned in respective recesses on the docking station and a removable sterilization seal respectively covers each of the recesses and thereby covers the respective bays with the ampules retained therein. Alternatively, the mouths of the ampules themselves may be covered with removable sterilization seals. This maintains the unused ampules in a sterile condition and also indicates to the operator that the respective bay is sterile and unused.

An additional feature is provided wherein the access mouth for each ampule that contains sterilization fluid is exteriorly exposed when the ampule is retained in its respective bay, and each ampule mouth is provided with a female line connection that is dimensioned and contoured for temporally receiving and securing thereto the male medical line connector such that the tubular tip is not only engaged with the sterilization fluid, but also the exposed end portions of the receded connection collar for the male medical line connector also engage the sterilization fluid whereby all connecting exposed surfaces of the male medical line connector are sterilized when the connector is docked. This embodiment further ensures that when the male medical line connector is reconnected to the patient is in a totally sterile condition. The chamber of each ampule may also include an annular array of inwardly protruding scrubbing finger webs for engaging and scrubbing exterior surfaces of the male connector.

BRIEF DESCRIPTION OF THE DRAWINGS

Other objects and advantages appear hereinafter in the following description and claims. The accompany drawings show, for the purpose of exemplification, without limiting the scope of the invention or the appended claims, certain practical embodiments of the present invention wherein:

DESCRIPTION OF PREFERRED EMBODIMENTS

Figure 1:
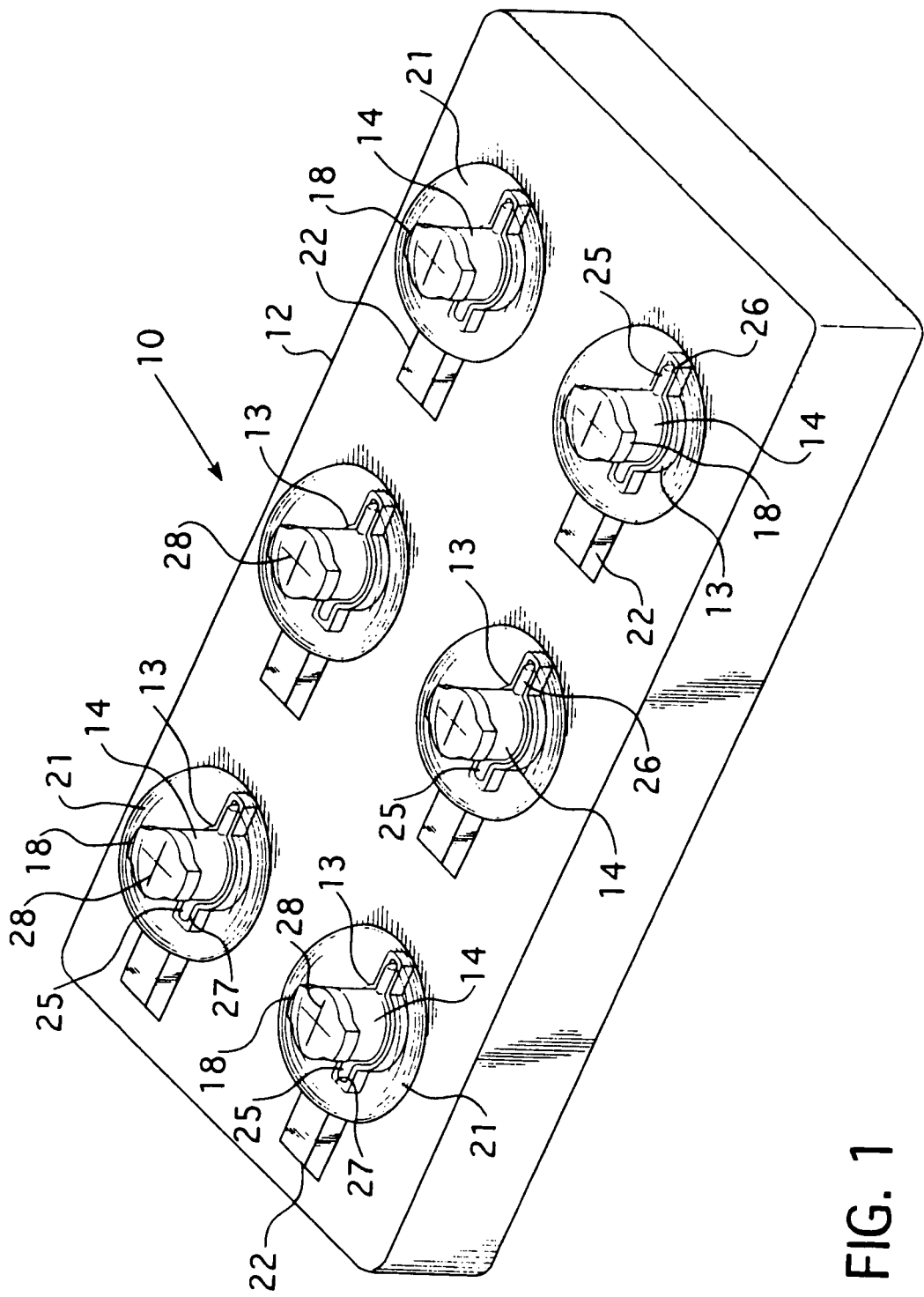
FIG. 1 is a perspective view of the docking station of the present invention showing the base housing with multiple docking bays respectively retaining ampules containing sterilization fluid.

Referring to the drawings, the docking station 10 is provided for docking male medical line connectors 11. The docking station 10 is comprised of a base housing 12, which in this instance is constructed of transparent plastic.

Base housing 12 is provided with a plurality of docking bays 13, each of which is dimensioned and contoured for respectively receiving and temporarily retaining ampules 14 containing sterilization fluid, liquid or gel alcohol. Each of the ampules 14 have a chamber 15 therein containing the sterilization fluid. The chambers 15 contain a foam liquid or gel absorbent material 16 for absorbing and retaining the sterilization fluid. Ampules 14 are each provided with a mouth 17 having a female medical line connector 18 (luer lock) exteriorly exposed when the ampules 14 are secured in one of the respective bays 13. The female medical line connector 18 is dimensioned and contoured for temporarily receiving and securing a male medical line connector 11 thereto with the tubular tip 20 thereof received in the absorbent material 16 thereby immersing the tip in sterilization fluid.

Dome shaped sterilization covers 21 are removable received over each of the bays 13. The covers 21 are also made of transparent plastic and have tabs 22 extending from a circumferential edge. Tabs 22 are provided with a light adhesive whereby each of the covers 21 may be readily removed individually by gripping the respective tab 22 and peeling it away from the upper surface 23 of base housing 12.

Each of the ampules 14 are received respectively in bays 13 by push insert and pull removal. Ampules 14 are respectively received in a socket 24 provided in each of the bays 13 for retaining the ampules 14 in bays 13 with a friction snap fit.

The ampules 14 are secured against rotation in bays 13 whereby the male connectors 11 may be rotatably connected with a conventional rotational luer lock to the ampules 14 while the ampules 14 remain secured in their respective bays 13. This is accomplished by providing the ampules 14 and the respective bays 13 with inter-engaging parts 25 whereby the ampules 14 are secured against rotation in the bays 13.

These inter-engaging parts 25 consist of wings 26 radially extending from the ampules 14, which in turn are received in corresponding grooves 27 of each bay 13.

The mouths 17 of each ampule 14 are sealed with a pierceable membrane 28 for piercing by the tubular tip 20 of male connector 11 in order to help maintain the internal cavity 15 of ampule 14 in a sterile condition and to also help prevent evaporation of the sterilization fluid, such as alcohol. When membrane 28 is pierced it is caused to annularly penetrate into chamber 15 and thereby secure and maintain absorbent material 16 therein.

The docking station 10 is slidably received in a holster 30, which in turn is removably secured to housing 31, which in turn is secured to a vertical surface or support in the form of IV pole 32. The holster 30, or an extra one thereof, may instead be secured to another or different adjacent surface.

Figure 2:
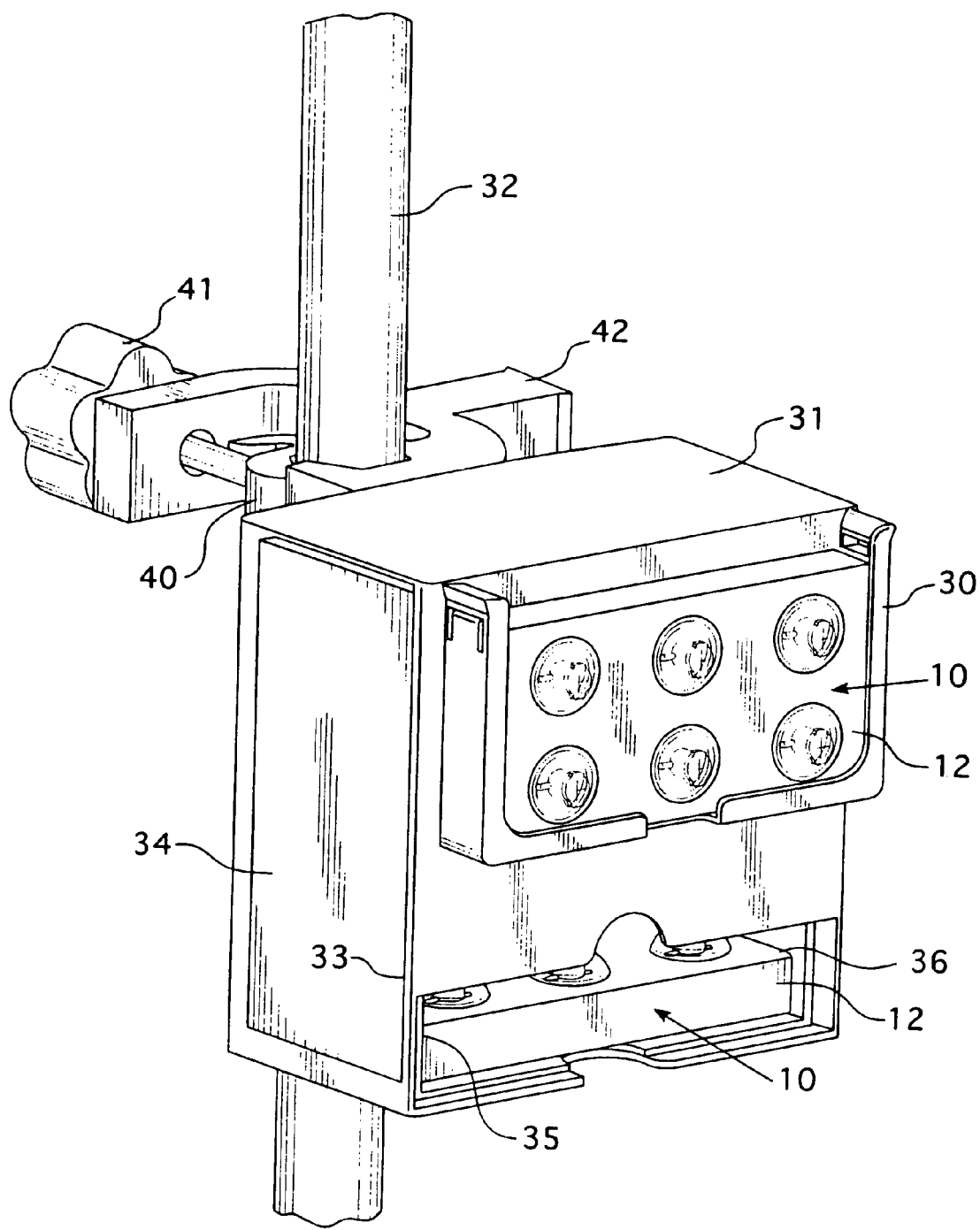
FIG. 2 is a perspective view of the docking station of the present invention as retained in a holster which in turn is secured to a vertically extending IV pole.
Figure 3:
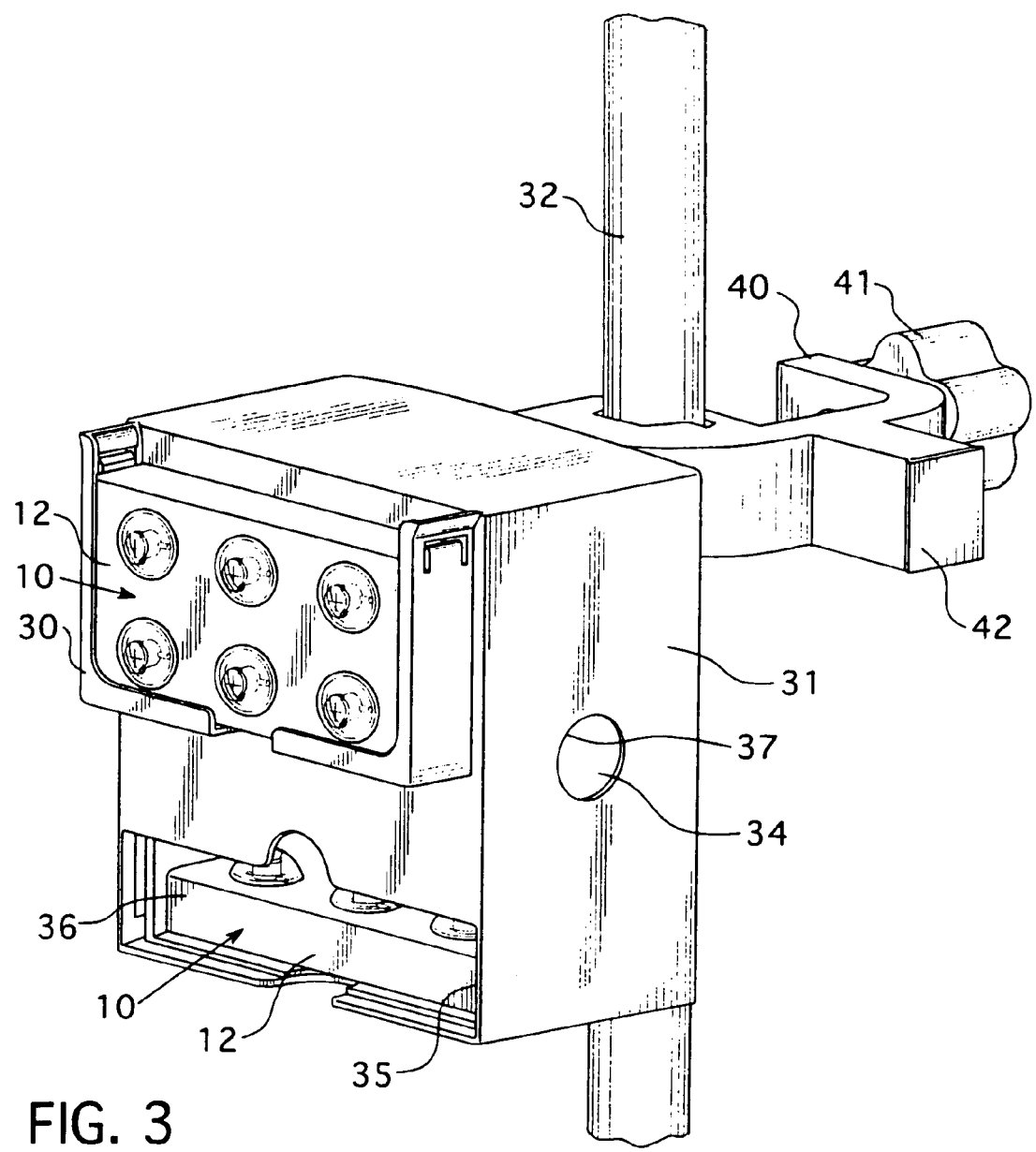
FIG. 3 is a perspective view illustrating the apparatus shown in FIG. 2 as viewed from the opposite side.
Figure 4:
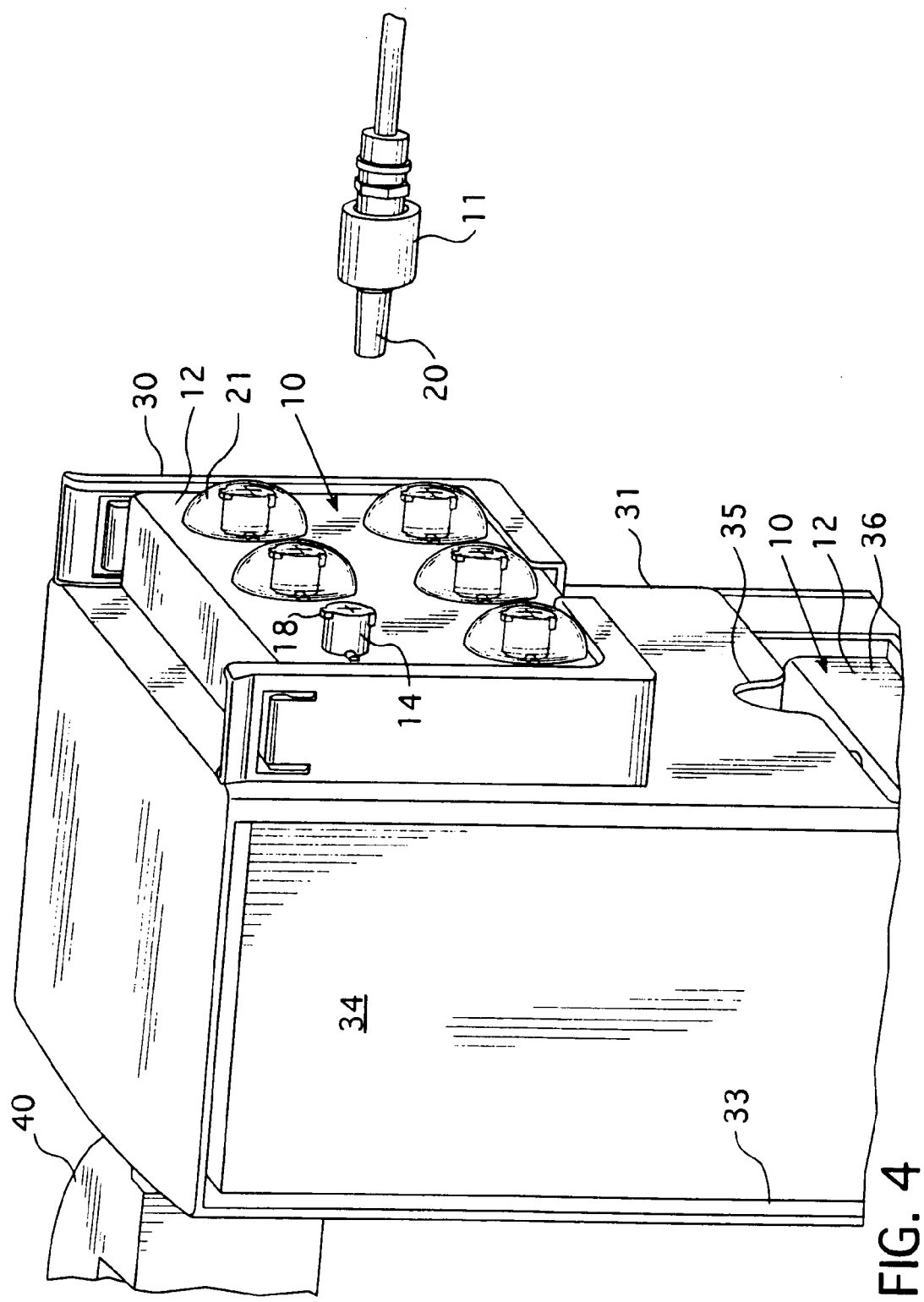
FIG. 4 is a perspective view illustrating a portion of the apparatus shown in FIG. 3 just prior to connection of a male medical line connector to an ampule retained in the docking station.
Figure 5:
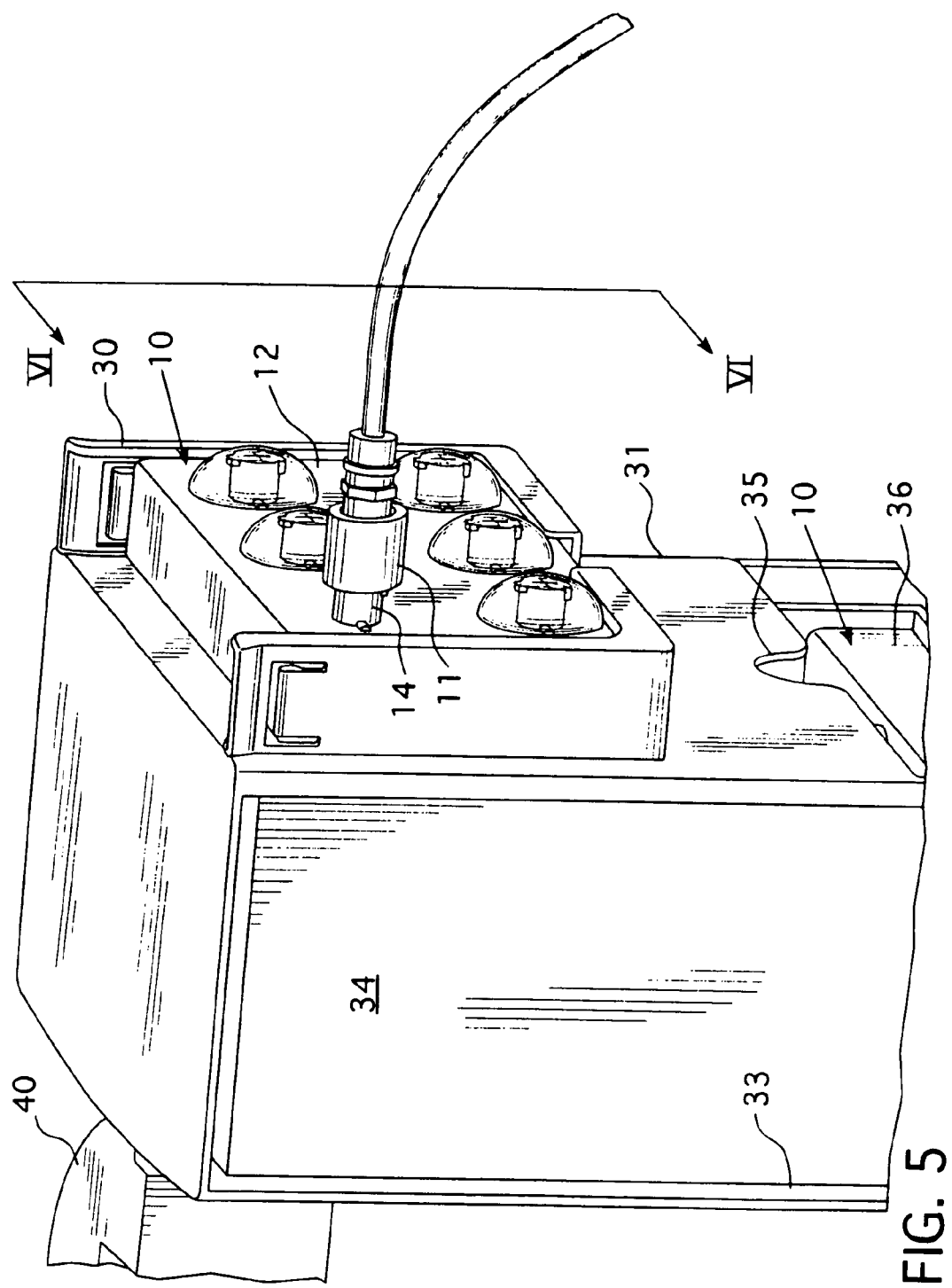
FIG. 5 is an illustration of the apparatus shown in FIG. 4 with the male medical line connectors engaged with an ampule retained in the docking station.
Figure 6:
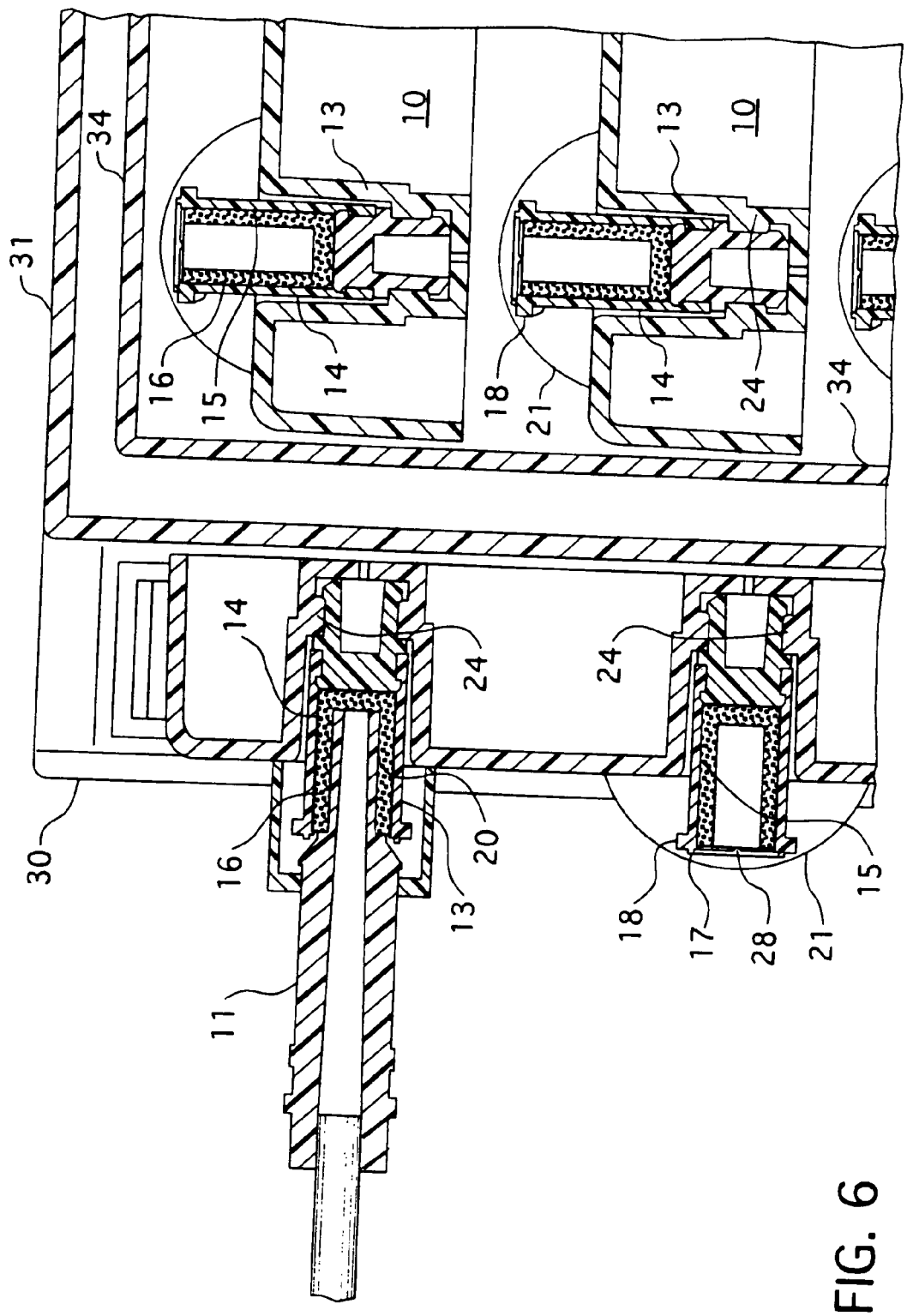
FIG. 6 is an enlarged sectional view of the apparatus illustrated in FIG. 5 as seen along section line VI-VI.

With particular reference to FIGS. 2 and 3, the housing 31 is provided with an internal cavity 33 for slidably receiving therein from the left side, as is best seen in FIG. 2, cartridge housing 34, which is open to the front and contains a stack of the docking stations 10. Housing 31 at the lower front thereof is provided with an opening 35 for thereby permitting access to the stack of docking stations whereby the bottom most docking station 36 in the stack may be removed and placed into the holster 30 when the docking station 10 previously contained therein has been depleted and is need of change.

As is best seen in FIG. 3, housing 31 on the right side is provided with an opening 37 to provide finger hole access in order to push cartridge housing 34 out to the left from the cavity 33 for removal once all of the docking stations 10 therein have been removed.

Housing 31 is secured to vertical IV pole 32 by means of the clamp 40 which is engaged and disengaged in a conventional fashion by rotating knob 41. Clamp 40 is also provided with an extension 42 for attaching or securing accessories, such as another holster 30.

Each of the bays 13 are provided in rows as indicated and, if desired, each of the rows of the base housing 12 may be designated by a different color coding in order to match a corresponding color coding on male medical line connectors 11 of a different type.

Other than the IV pole 32 and parts of the clamp 40, the entire system may be manufactured of plastics.

Referring next to FIGS. 7 through 10 another embodiment of the docking station of the present invention is illustrated which prevents accidental reuse of the ampules 14. In this embodiment, the ampules 14 are secured against rotation in the clockwise direction in the respective bays 13 to facilitate threadable connection of a male medical line connector 11. However, the respective ampules 13 are permitted to freely rotate in the counterclockwise direction in their respective bays 13 to prevent disconnection of a male medical line connector 11 from its respective connected ampule 14 while retained in its bay 13. This is accomplished by the inter-engaging parts 25. The inter-engaging parts 25 include the laterally extending wings 26 on opposite sides of the ampules 14 and these extending wings 26 are respectively received in corresponding recesses 27' of bays 13. The recesses 27' have bottom ramp surfaces 50 which ramp upwardly or outwardly on an incline as they progress in the counterclockwise direction. These ramp surfaces 50 engage the bottom edges 51 of wings 26 whereby when the ampules 14 are rotated in the counterclockwise direction, as by rotating a connected male medical line connector 11 for disconnection, the bottom edges 51 of wings 26 which are engaging ramp surfaces 50 cause the ampule 14 to be pushed upwardly and outwardly out of its respective bay 13 when the ampule is rotated counterclockwise. This forces the operator to actually remove the connected ampule from the docking station 10 and to thereafter manually disconnect the medical line connector 11 from the expelled ampule 14 and to thereafter discard the used ampule 14. This prevents accidental reuse of a sterilization ampule 14. As the bottom edges 51 of wings 26 ride upwardly and outwardly on ramp surfaces 50 when ampule 14 is turned counterclockwise, this forces the ampule 14 to disengage from its snap in connection in bay 13 as indicated at 24, thereby forcibly eject ampule 14 from its respective bay 13.

Figure 7:
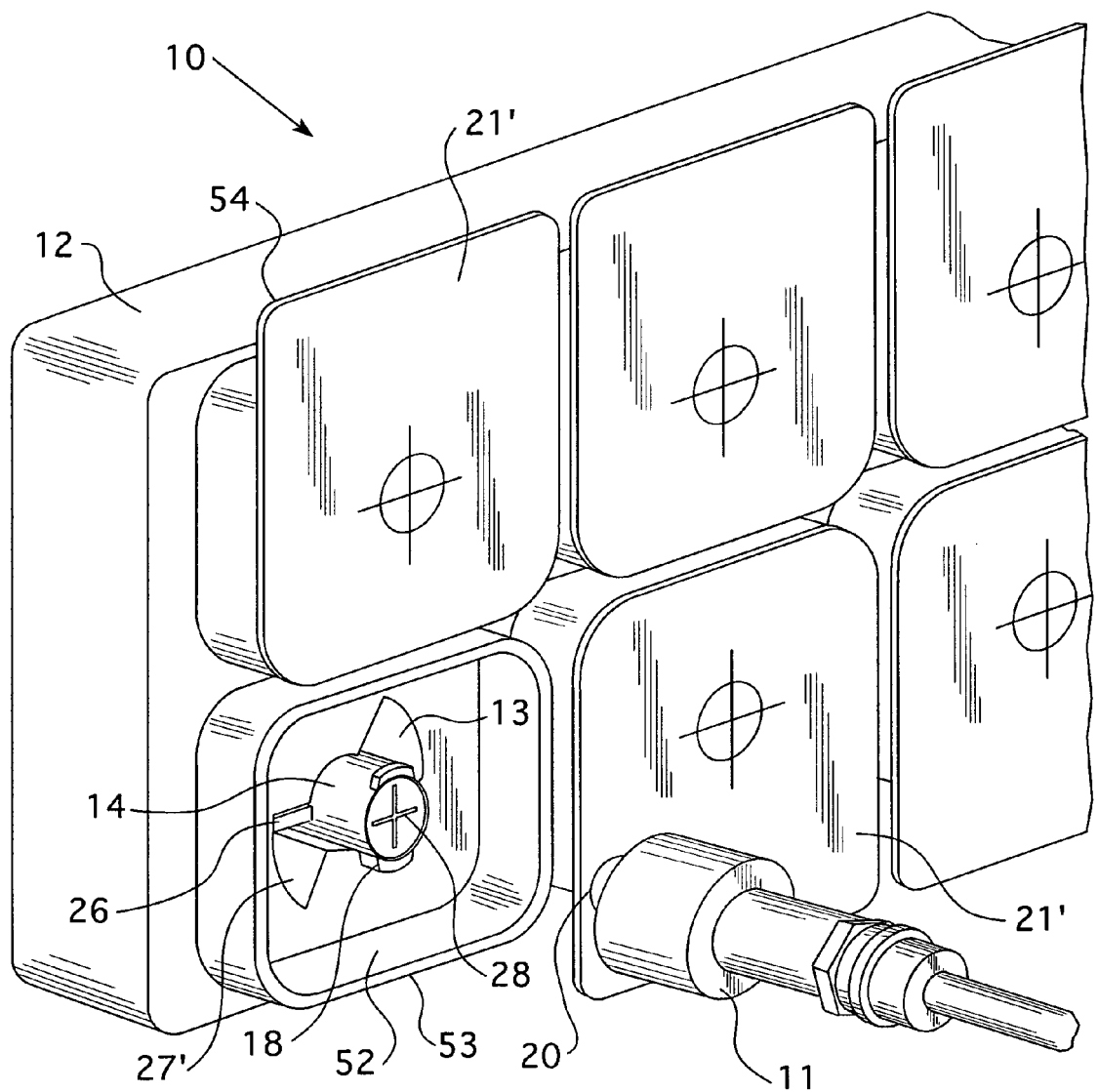
FIG. 7 is a perspective view illustrating a portion of a modified embodiment of the docking station of the present invention which incorporates structure that causes forced removal of the sterilization ampules from the docking station after use and further illustrates removable sterilization seals covering respective bays before use of the respective ampules retained therein.
Figure 8:
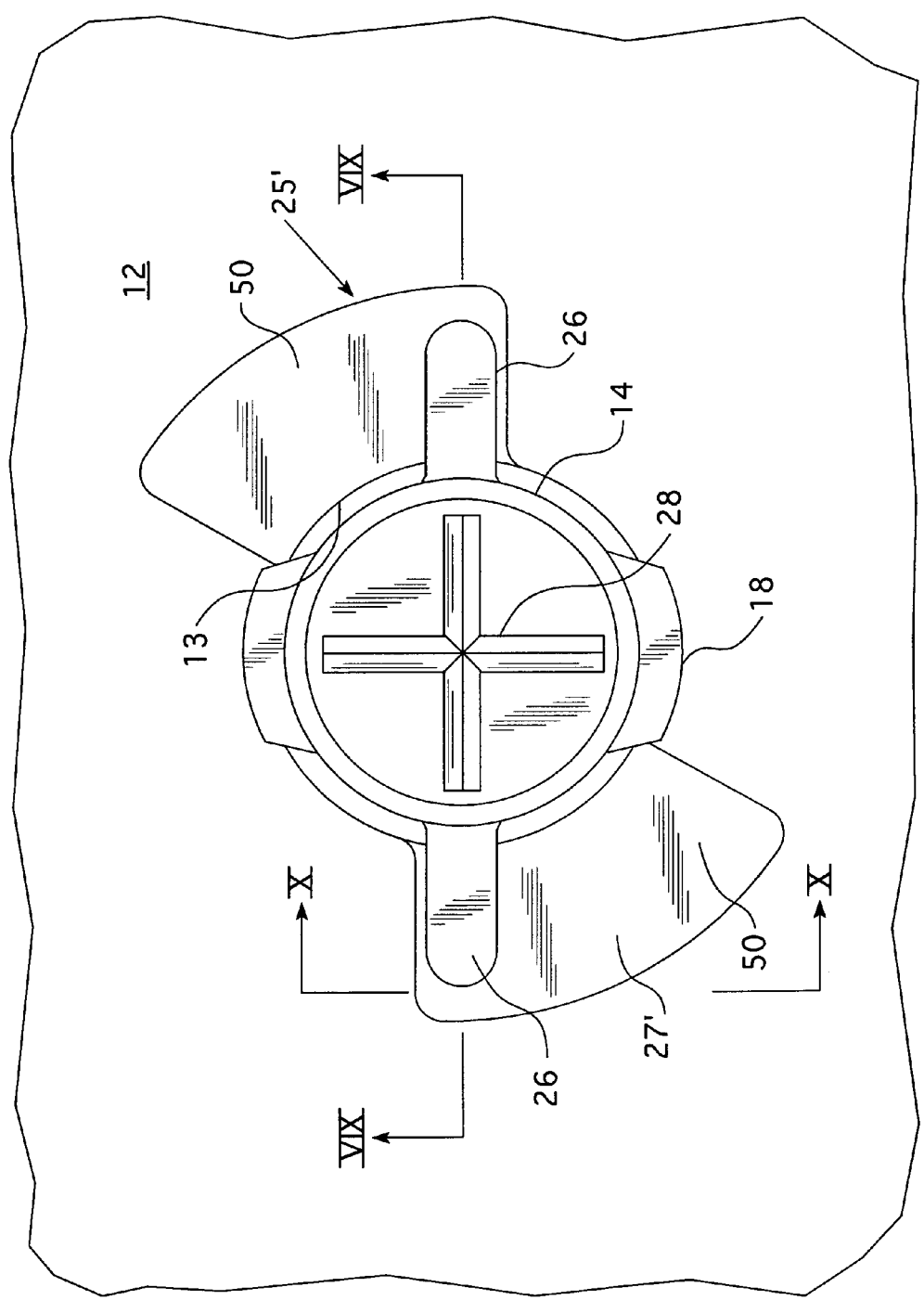
FIG. 8 is an enlarged plan view of one of the docking bays with a sterilization ampule retained therein of the docking station shown in FIG. 7.
Figure 9:
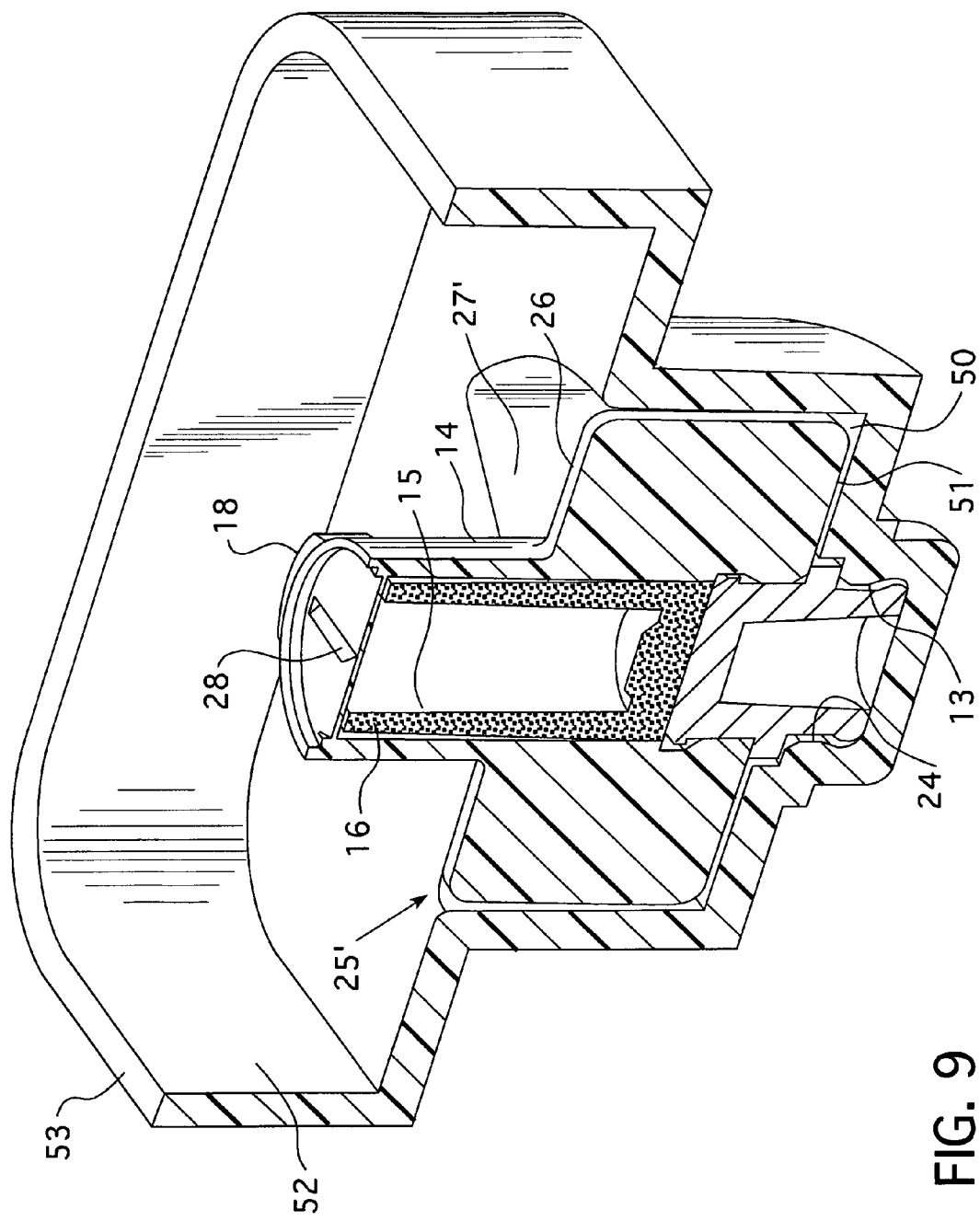
FIG. 9 is a perspective cross sectional view of the combination docking bay and sterilization ampule contained therein as shown in FIG. 8 and as seen along section line IX-IX.
Figure 10:
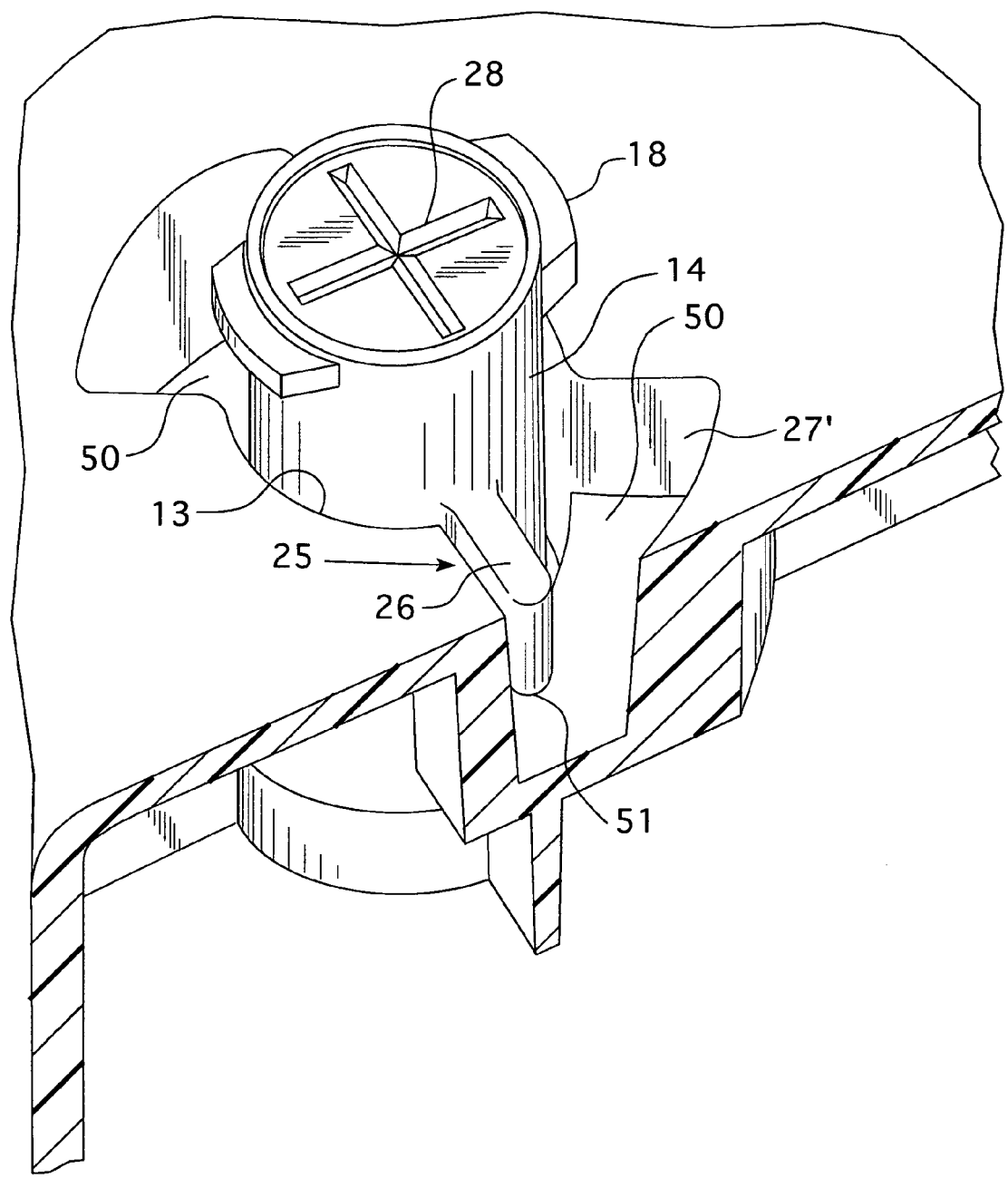
FIG. 10 is a perspective cross sectional view of the combination docking bay and sterilization ampule contained therein as seen along section line X-X of FIG. 8.
Figure 11:
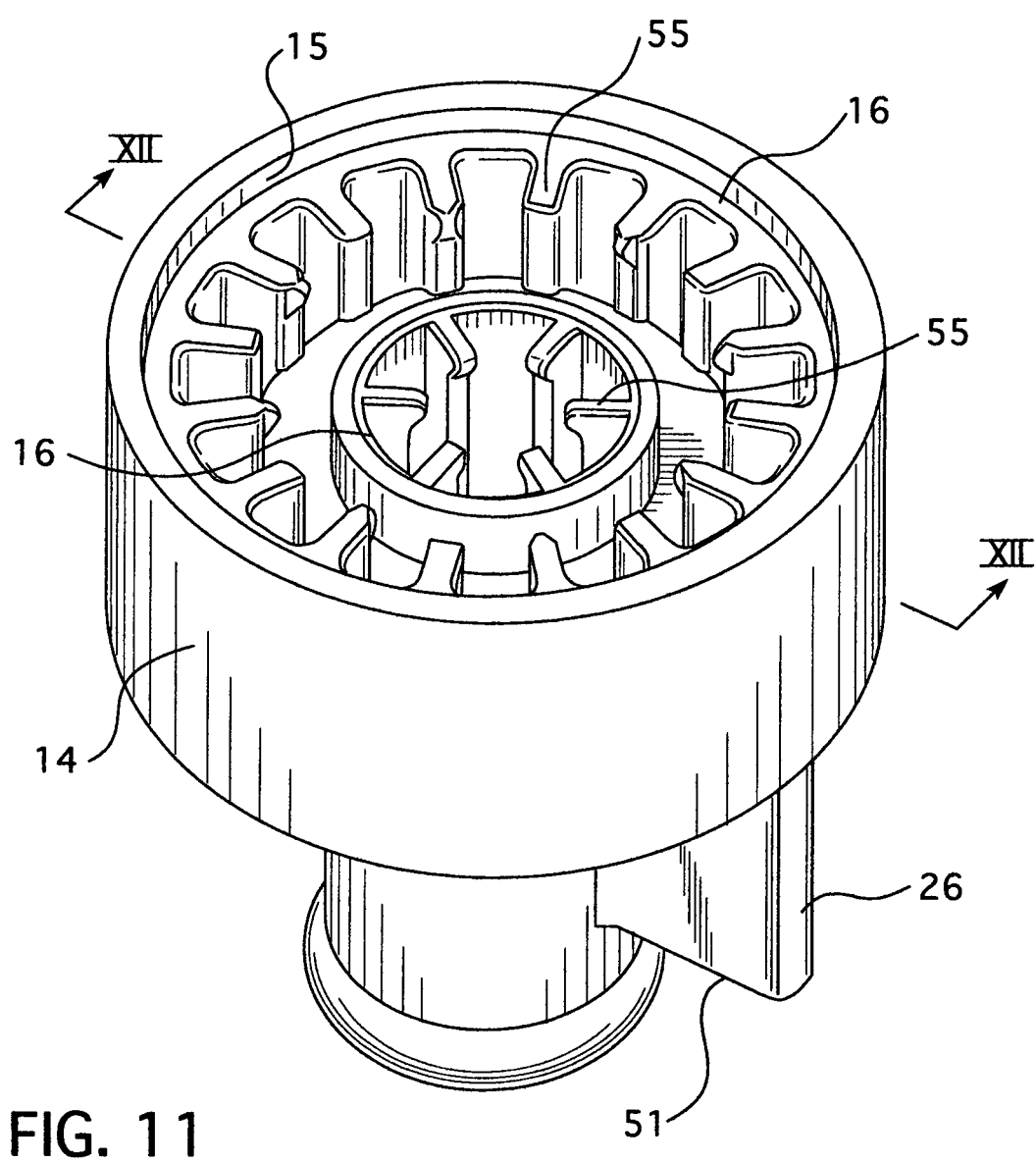
FIG. 11 is an isometric view of another embodiment of the sterilization ampule of the present invention.
Figure 12:
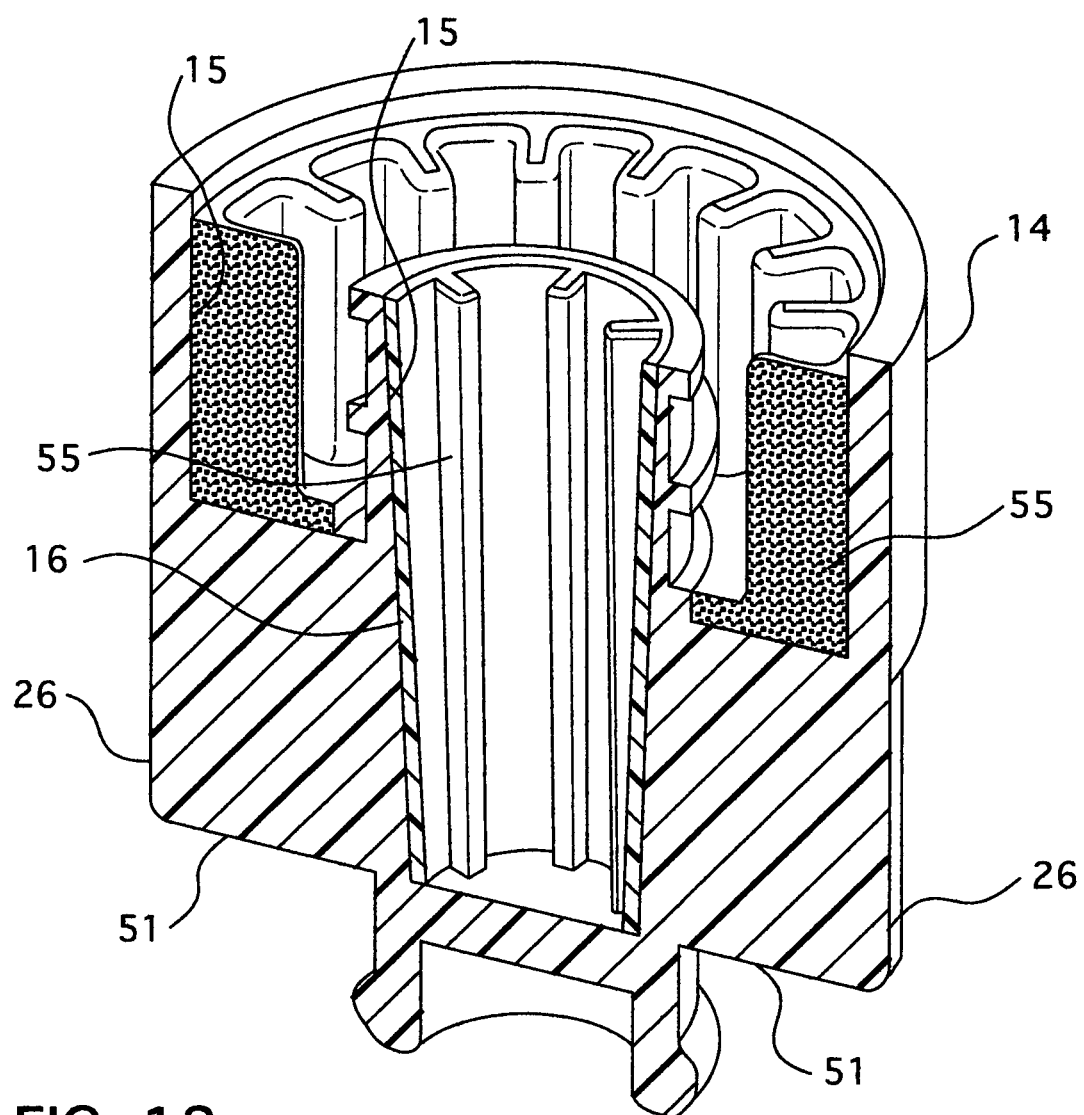
FIG. 12 is an isometric cross sectional view of the ampule shown in FIG. 11 as seen along section line XII-XII of FIG. 11.

Instead of the sterilization sealing domes 21 as illustrated in FIG. 1, sterilization seals 21' are provided in this embodiment. Each of the bays 13 with their respective ampules 14 retained therein are positioned in respective recesses 52 as seen in FIGS. 7 and 9. The upper edges 53 and recesses 52 are covered with a foil seal 21' which is adhered to edges 53 to retain the content thereunder in sterilized condition. Seals 21' are easily removed by grasping an exposed edge 54 thereof and peeling them off the upper edge 53 of recesses 52.

Referring next to FIGS. 11 through 15, another embodiment of the present invention is illustrated. In this embodiment the probe tip 20 of male medical line connector 11 is not only sterilized when docked, but in addition the receded concentric connection collar 52 also has its exposed end portions 53 and exterior portions 54 engaged with the sterilization fluid contained within chamber 15 of ampule 14. Accordingly, all of the exposed end surfaces of the tubular tip 20 and the connection collar 52 are fully treated with sterilization fluid and sterilized during the docking procedure.

The chamber 15 includes an annular array of inwardly protruding scrubbing finger webs 55 for engaging and scrubbing interior surfaces of the tip 20 and the connection collar 52. These scrubbing finger webs 55 are constructed of any suitable material, such as an elastomeric plastic or rubber, absorbing sponge or the like to flexibly engage and scrub the exterior surfaces of the collar 52 and the probe tip 20.

Figure 13:
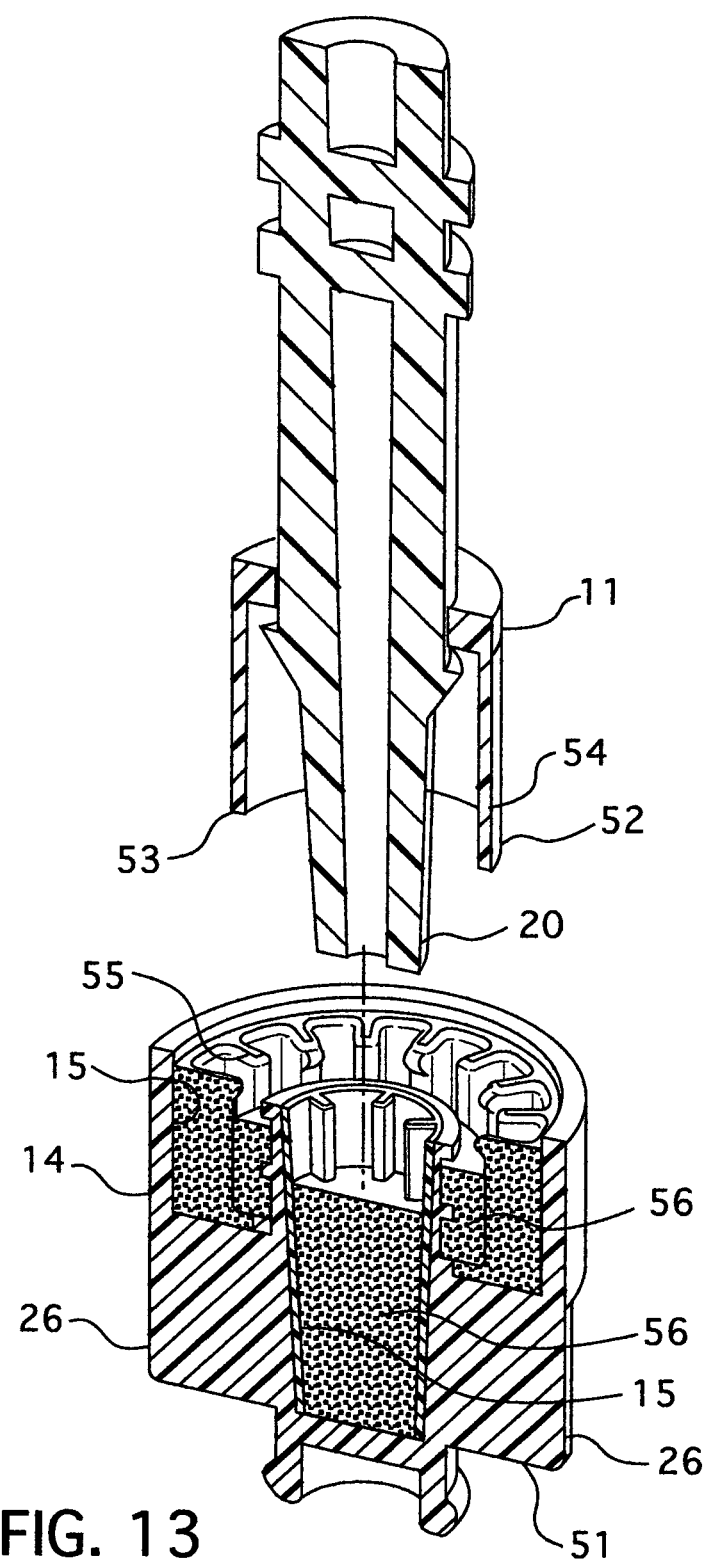
FIG. 13 is an isometric cross sectional view of the ampule shown in FIG. 12 with compressible sponge shown in bottom portions thereof, together with a male medical line connector shown in mid cross section prior to insertion into the ampule.
Figure 14:
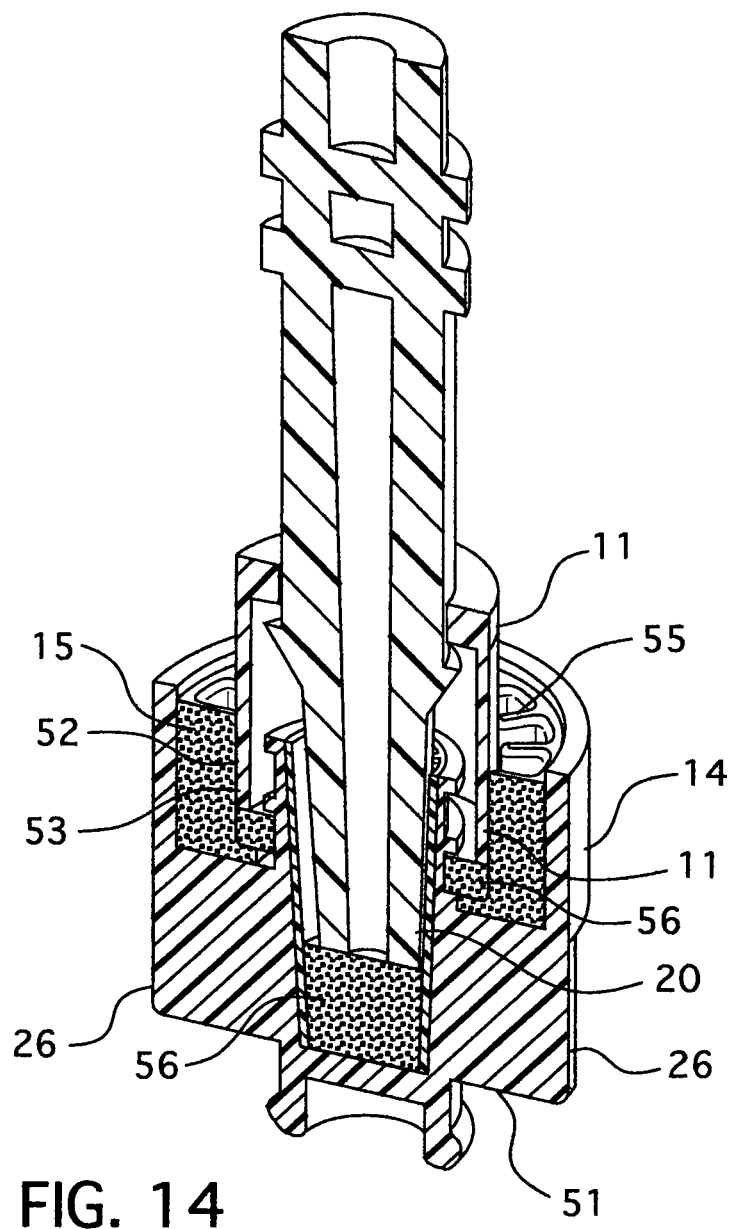
FIG. 14 is an isometric view in mid cross section illustrating the combination shown in FIG. 13 with the male medical line connector seated within the ampule for sterilization.

A reservoir of the sterilization fluid may also be retained in the bottom portion of the chamber 15 by compressible sponge 56 as illustrated in FIGS. 13 and 14. The sponge 56 accordingly absorbs the sterilization fluid and expels the fluid upon compression caused by insertion of the medical male line connector 11.

Figure 15:
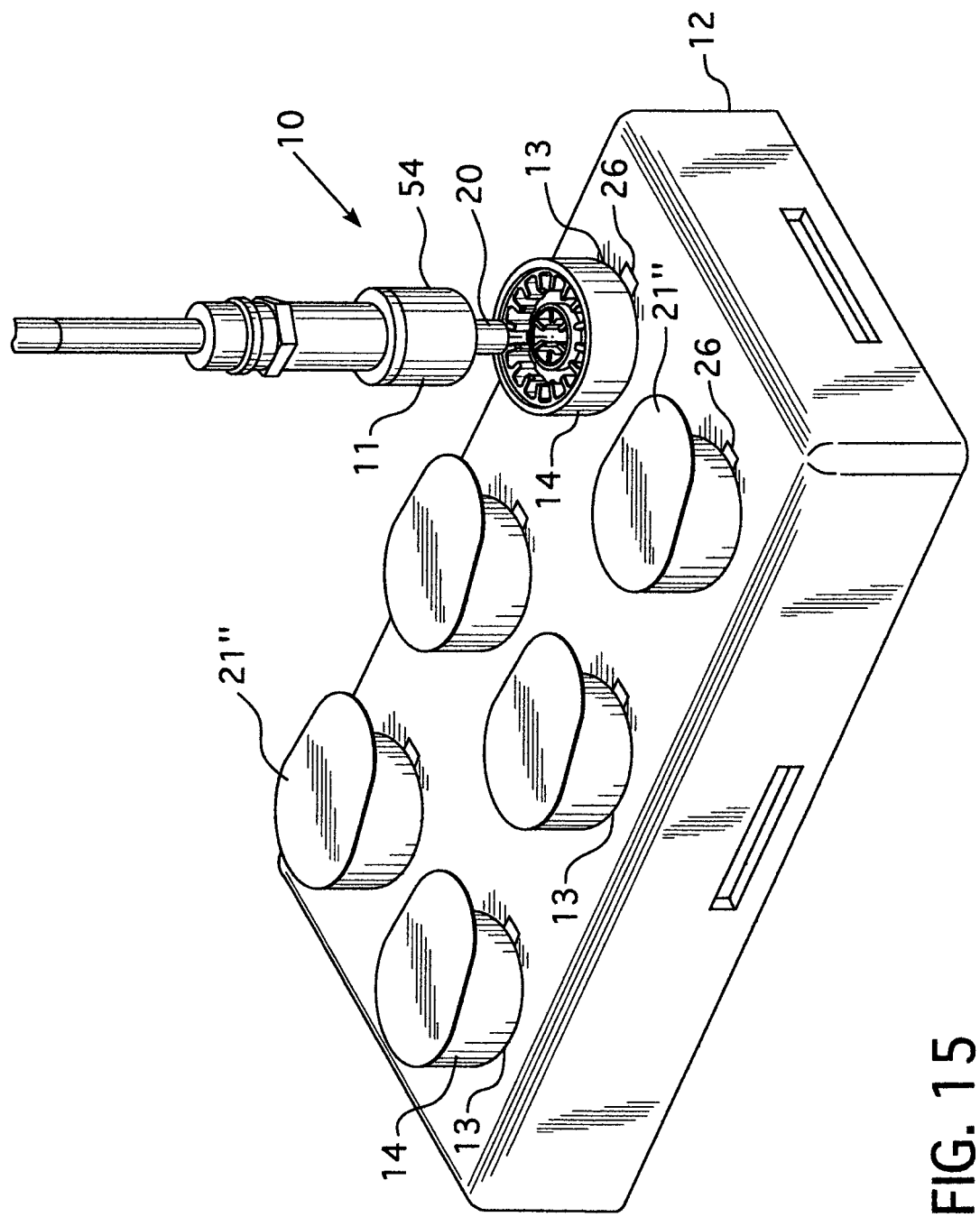
FIG. 15 is an isometric view of the embodiment of the docking station of the present invention incorporating the combination male medical line connector and sterilization ampules shown in FIGS. 13 and 14.

FIG. 15 illustrates the combination shown in FIGS. 11 through 14 showing the ampules 14 seated in respective bays 13 of base housing 12. Like embodiments are all designated with the same reference numerals.

In the embodiment of FIG. 15, the removable seals 21" seal over the upwardly open mouths of the respective ampules 14 instead of covering the respective bays 13 as shown in previous embodiments.

We claim:

1. A docking station for a male medical line connector, comprising:
    a base housing having a docking bay dimensioned and contoured for receiving and temporarily retaining an ampule containing a sterilization fluid;
    said ampule having a chamber therein containing the sterilization fluid and an access mouth exteriorly exposed when said ampule is retained in said bay, said mouth having a female medical line connection dimensioned and contoured for temporarily receiving and securing the male medical line connector thereto with a tubular tip of said male connector thereby exposed to said sterilization fluid;
    said ampule secured against rotation in a clockwise direction in said bay to facilitate threadable connection of the male medical line connector, and permitted to freely rotate in a counterclockwise direction in said bay to prevent disconnection of the male medical line connector therefrom while the connected ampule is retained in said bay, whereby said ampule is dislodged from said bay with said male medical line connector attached; and
    said ampule and said bay having inter-engaging parts whereby said ampule is secured against rotation in the clockwise direction in said bay and permitted to freely rotate in the counterclockwise direction.

2. The docking station of claim 1, wherein said inter-engaging parts include laterally extending wings on said ampule and corresponding recesses in said bay receiving said wings, said recesses having ramp surfaces for engaging bottom edges of said wings and thereby forcing said ampule out of said bay when rotated in the counterclockwise direction.

3. The docking station of claim 1, wherein said bay is positioned in a recess with a removable sterilization seal covering said recess and thereby covering said bay with said ampule retained therein.

4. A docking station for male medical line connectors, comprising:
    a base housing securable to a normally stationary surface and having a plurality of docking bays, each of which is dimensioned and contoured for respectively receiving and temporarily retaining ampules containing a sterilization fluid;
    each of said ampules having a chamber therein containing the sterilization fluid and an access mouth exteriorly exposed when said ampule is secured in one of said bays, said mouth having a female medical line connection dimensioned and contoured for temporarily receiving and securing one of the male medical line connectors thereto with a tubular tip of said one of said male connectors thereby exposed to said sterilization fluid;
    said ampules secured against rotation in a clockwise direction in said bays to facilitate threadable connection of the male medical line connectors, and permitted to freely rotate in a counterclockwise direction in said bays to prevent disconnection of said male medical line connectors therefrom while the connected ampules are retained in said bays, whereby said ampules are dislodged from said bays with said male medical line connectors attached; and
    said ampules and said bays having inter-engaging parts whereby said ampules are secured against rotation in the clockwise direction in said bays and permitted to freely rotate in the counterclockwise direction.

5. The docking station of claim 4, wherein said inter-engaging parts include laterally extending wings on said ampules and corresponding recesses in said bays receiving said wings, said recesses having ramp surfaces for engaging bottom edges of said wings and thereby forcing said ampules out of said bays when rotated in the counterclockwise direction.

6. The docking station of claim 4, wherein said bays are positioned in respective recesses with removable sterilization seals respectively covering said recesses and thereby covering said bays with said ampules retained therein.

* * * * *